United States Patent [19]

Cooper et al.

[11] Patent Number: 5,130,432
[45] Date of Patent: Jul. 14, 1992

[54] PROCESS FOR PREPARING CYCLIC AMINES AND INTERMEDIATE PRODUCTS THEREOF

[75] Inventors: Gary F. Cooper, Portola Valley; Michael G. Martin, San Francisco, both of Calif.

[73] Assignee: Syntex (U.S.A.) Inc., Palo Alto, Calif.

[21] Appl. No.: 633,636

[22] Filed: Dec. 21, 1990

[51] Int. Cl.$^5$ ............................................. C07D 515/02
[52] U.S. Cl. .................................... 546/114; 546/192; 546/236; 548/122; 548/570
[58] Field of Search ............... 546/114, 236, 192; 548/122, 570

[56] References Cited

U.S. PATENT DOCUMENTS 4,279,918 7/1981 Eistetter et al. ............... 548/400 X

FOREIGN PATENT DOCUMENTS 0404115 6/1990 European Pat. Off. .

OTHER PUBLICATIONS

Alker, D. et al. The Direct Synthesis of the Cyclic Sulphamidate of (s)-Prolinol: Simultaneous N-Protection and Activation Towards Nucleophilic Displacement of Oxygen Tetrahedron: *Asymmetry* 1990; 1(12): 877–880.
Zubovic, Z. et al. Synthesis and antiarrhythmic Activity on N-aryl Alkylenediamines *Eur. J. Med. Chem.— Chim. Ther.* 1986; 21(5): 370–378.
Noda, Y. A New Imino Acid Derived from L-serine O-sulfate *Bull. Chem. Soc. Japan* 1967; 40(6): 1554.
Lyle, T. A. et al. Fluoride-Induced Formation and Ring Opening of Cyclid Sulfamates from Hydroxy Triflamides. Synthetic and Mechanistic Studies *J. Am. Chem. Soc.* 1987: 109: 7890–7891.

*Primary Examiner*—Joseph Paul Brust
*Assistant Examiner*—Jacqueline Haley

*Attorney, Agent, or Firm*—Wayne Montgomery; Derek P. Freyberg; Tom M. Moran

[57] ABSTRACT

A process for preparing a cyclic amine of Formula I

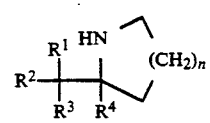

(I)

in which
$R^1$ is phenyl, optionally substituted by 1 to 3 lower alkoxy groups;
$R^2$, $R^3$ and $R^4$ are independently hydrogen or lower alkyl; and
n is 1 or 2, comprises
(1) converting an aminoalcohol of Formula III

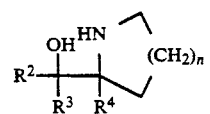

(III)

to a dioxooxathiazolidine of Formula II

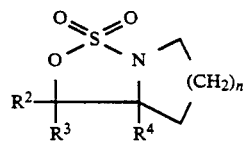

(II)

in which $R^2$, $R^3$, $R^4$ and n are as defined above; and
(2) reacting the dioxooxathiazolidine of Formula II with an organometallic nucleophile, $R^1M^*$, wherein $R^1$ is as defined above, and hydrolyzing the resulting sulfamate salt.

8 Claims, No Drawings

1

PROCESS FOR PREPARING CYCLIC AMINES AND INTERMEDIATE PRODUCTS THEREOF

FIELD OF THE INVENTION

This invention relates to a process for preparing cyclic amines.

BACKGROUND OF THE INVENTION

Optically active amines are useful in asymmetric synthesis of organic compounds. For example, optically active bases such as (+)- and (−)-ephedrine, (−)-2-amino-1-butanol, (+)- and (−)-α-methylbenzylamine, (+)-amphetamine or (+)-deoxyephedrine are used extensively as resolving agents (Jacques, J., Collet, A. and Wilen, S. H. 1981. *Enantiomers, Racemates, and Resolutions*, 253–255. New York: John Wiley & Sons). In addition, chiral amines are useful in the preparation of asymmetric catalysts (*Asymmetric Synthesis*, 27–29. Ed. Morrison, J. D. Orlando, Fla.: Academic Press, Inc.).

Optically active amines are also of use as intermediates in the preparation of pharmaceutical agents and are of values as therapeutic agents themselves. For example, many biogenic amines and the various synthetic analogs thereof are β-arylethylamines, e.g., dopamine when aryl is 3,4-dihydroxyphenyl. Substitution at the α- or β-carbon of the ethylamine parent structure creats an asymmetric center and it is usual for one of the two stereoisomers to possess the greater activity.

Dopamine, a catecholamine with both adrenergic and dopaminergic receptor activity, is an important central neutrotransmitter. In addition, exogenous dopamine has found use clinically in the treatment of shock and chronic refractory heart failure (Goldberg, L. I., 1974, N. Engl. J. Med., 291, 707). Dopamine acts at $\beta_1$-receptors in the heart to exert cardiostimulatory effects and at $\alpha_1$-receptors in the vasculature to exert vasoconstriction. Dopamine also acts both centrally and peripherally at discrete dopaminergic receptors. Current dogma delineates dopaminergic receptors into two subclassifications, i.e., $DA_1$ and $DA_2$ receptor subtypes. Peripherally, $DA_1$ receptors mediate vasodilitation of vascular smooth muscle and $DA_2$ receptors mediate inhibition of norepinephrine release from postganglionic sympathetic nerves (Goldberg, L. I. and Kohli, J. D., 1983, Tends Pharmacol. Sci. 4, 64).

The β-phenylethylamine parent structure of the sympathomimetic amines permits substitutions at the aromatic ring, the α- and β-carbon atoms, and the terminal amino group. Such substitutions may affect activity or receptor selectivity. For example, hydroxy substitution of the β-carbon can significantly enhance both α- and β-adrenergic receptor activity, N-substituted amines may exhibit greater β-adrenergic receptor activity, and substitutions on the α-carbon may block oxidation by monoamine oxidase thus enhancing the duration of action and oral activity (Gilman, A. G., Goodman, L. S., Rall, T. W. and Murad, F. 1985. *The Pharmacological Basis of Therapeutics*, 148–150. 7th ed. New York: Macmillan Publishing Company).

Several dopaminergic agonists have been described which act at $DA_1$ and $DA_2$ receptors but possess little or no adrenergic receptor activity. In that such compounds exhibit low activity at α- and β-adrenergic receptors but retain activity at dopaminergic receptors, they have potential for use as anti-hypertensives or as afterload reducing agents in the treatment of congestive heart failure.

In addition to those optically active amines which are themselves useful as therapeutic agents, certain amines are useful as intermediates in the synthesis of pharmaceutically useful compounds. For example, (R)-2-(3,4-dimethoxybenzyl)pyrrolidine, disclosed in U.S. Pat. No. 4,279,918, is a key intermediate in the synthesis of certain orally active benzylpyrrolidene $DA_1/DA_2$ receptor agonists, described in U.S. patent applications Ser. Nos. 07/369,366, titled "Bis(benzylpyrrolidine) Derivatives as Dopamine Agonists", filed Jun. 21, 1989, and 07/428,577, titled "Benzylpyrrolidine Derivatives as Dopamine Agonists", filed Oct. 30, 1989. Of the compounds described therein, (R)-2-(3,4-dihydroxybenzyl)-1-[6-(N-(3,4-dihydroxyphenethyl)-N-propylamino)hexyl]pyrrolidine and (R,R)-1,6-bis[2-(3,4-dihydroxbenzyl)pyrrolidin-1-yl]hexane are of particular interest.

Traditionally the preparation of optically active amines has been difficult and the process usually involves displacement of an activated optically active hydroxy group. Naturally, amino acids are a good source for optically active amines as starting materials. The amino acid may be reduced to form an aminoalcohol or larger molecules may be constructed with the use of various Grignard reagents, a step that necessitates the protection of the amine function of the amino acid (see processes described in U.S. patent applications Ser. Nos. 07/369,366 and 07/428,577).

The disclosures of these and other documents referred to throughout this application are incorporated herein by reference.

SUMMARY OF THE INVENTION

A first aspect of this invention is a process for preparing a cyclic amine of Formula I

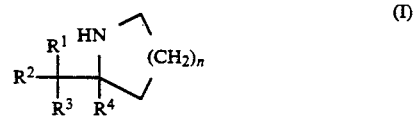

in which $R^1$ is phenyl, optionally substituted by 1 to 3 lower alkoxy groups;

$R^2$, $R^3$ and $R^4$ are independently hydrogen or lower alkyl; and n is 1 or 2, which comprises (1) converting an aminoalcohol of Formula III

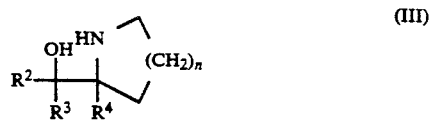

to an dioxooxathiazolidine of Formula II

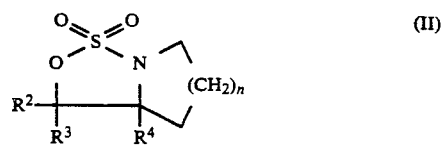

in which $R^2$, $R^3$, $R^4$ and n are as defined above; and (2) reacting the dixooxathiazolidine of Formula II with an organometallic nucleophile, $R^1M^*$, wherein $R^1$ is as defined above, and hydrolyzing the resulting sulfamate.

A second aspect of this invention is the dioxooxathiazolidine of Formula II

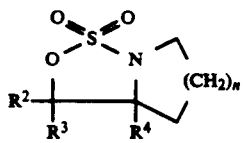

in which
$R^2$, $R^3$ and $R^4$ are independently hydrogen or lower alkyl; and
n is 1 or 2.

DETAILED DESCRIPTION OF THE INVENTION

Definitions

Unless otherwise stated, the following terms used in the specification and claims have the meanings given below:

"Alkyl" means a straight, branched, or cyclic saturated hydrocarbon radical having from 1 to 10 carbon atoms, e.g., methyl, ethyl, i-propyl, n-propyl, n-butyl, cyclopropylmethyl, pentyl, cyclohexyl, heptyl and the like.

"Alkoxy" means the radical —OR wherein R is "alkyl" as defined above, e.g., methoxy, ethoxy, i-propoxy, n-propoxy, n-butoxy, pentyloxy, hexyloxy and the like.

"Lower" modifies "alkyl" and "alkoxy" and refers those radicals containing 1 to 4 carbon atoms.

"Organometallic nucleophile", $R^1M^*$, has the meaning conventionally associated with it in synthetic organic chemistry, i.e., a compound in which an organic group is bonded to a metal, $M^*$, such as magnesium, zinc, lithium, and the like, and is capable of initiating a nucleophilic substitution reaction. Such compounds include $R^1MgX$, $R^1ZnX$, $R^1_2Zn$, $R^1Li$, and the like.

"Optional" or "optionally" means that the subsequently described event or circumstance may or may not occur, and that the description includes instances where said event or circumstance occurs and instances in which it does not. For example, "optionally substituted phenyl" includes unsubstituted and substituted phenyl radicals.

Compounds that have identical molecular formulae but differ in the nature or sequence of bonding of their atoms or in the arrangement of their atoms in space are termed "isomers". Isomers that differ in the nature or sequence of bonding of their atoms are termed "constitutional isomers". Isomers that differ only in the arrangement of their atoms in space are termed "stereoisomers". Stereoisomers that are not mirror images of one another are termed "diastereomers" and stereoisomers that are mirror images are termed "enantiomers" or sometimes "optical isomers". Stereoisomers that are superimposable upon their mirror images are termed "achiral" and those not superimposable are termed "chiral". A carbon atom bonded to four different groups is termed a "chiral center" or alternatively an "asymmetric carbon".

When a compound has a chiral center, a pair of enantiomers of opposite chirality is possible. An enantiomer may be characterized by the absolute configuration of its chiral center and described by the R- and S-sequencing rules of Cahn and Prelog (i.e., as (R)- and (S)-isomers) or by the manner in which the molecule rotates the plane of polarized light and designated as dextrorotatory or levorotatory (i.e., as (+)- and (−)-isomers, respectively). A compound may exist as either an individual enantiomer or as a mixture thereof. Conventions for stereochemical nomenclature, methods for the determination of sterochemistry and the separation of stereoisomers are well-known in the art (see discussion in Chapter 4 of "Advanced Organic Chemistry", 3rd edition, March, Jerry, John Wiley and Sons, New York, 1985). Unless indicated otherwise, the description or naming of a particular compound of Formula I, II or III in the specification and claims is intended to include all possible enatiomers and mixtures, racemic or otherwise, thereof.

Starting Materials and Purification

In general, the aminoalcohols of Formula III and other reagents utilized in preparing compounds of Formula II are known to those of ordinary skill in the art or their synthesis from known compounds is well described (*Organic Synthesis*, 65: 173, Vedejs, E., John Wiley and Sons, New York, 1987) Syn., 65, 173). For example, (R)- and (S)-2-pyrrolidinemethanol, aminoalcohols of Formula III in which $R^2$, $R^3$, and $R^4$ are hydrogen and n is 1, are commercially available or may be prepared by reduction of the corresponding amino acids, D- and L-proline. Such reductions of amino acids may be accomplished with reducing agents such as lithium aluminum hydride, boron trifluoride/diborane, boron trifluoride/diborane methylsulfide complex, lithium borohydride/chlorotrimethylsilane, preferably lithium aluminum hydride, in solvents such as tetrahydrofuran, methyltetrahydrofuran, etc., preferably THF, under standard reduction conditions. A detailed description of this procedure for the preparation of (R)-2-pyrrolidinemethanol is given in Example 1.

The starting materials, the intermediates of Formula II, and the products of Formula I may be isolated and/or purified, if desired, using conventional techniques of organic synthesis, including but not limited to filtration, distillation, crystallization, chromatography, and the like. They may be characterized using conventional means such as physical constants and spectral data.

The Process

Compounds of Formula I may be prepared by the reaction sequence shown below

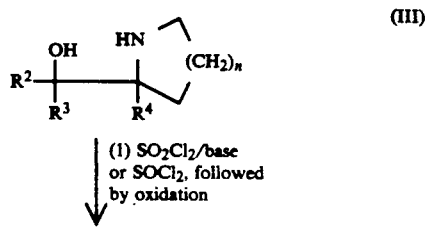

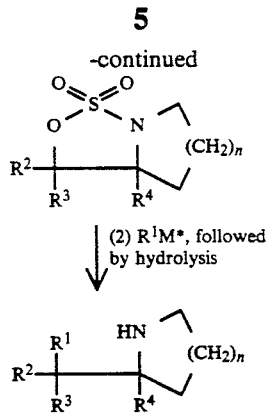

Step 1

A 2,2-dioxo-1,2,3-oxathiazolidine of Formula II may be prepared by reacting an aminoalcohol of Formula III with sulfuryl chloride in the presence of a suitable base, such as an organic amine, e.g., triethylamine or, preferably, pyridine. The reactants are mixed in a suitable aprotic solvent, such as methylene chloride, 1,2-dichloroethane, carbon tetrachloride, benzene, toluene or pyridine, and stirred for 5 to 60 minutes at or below −60° C. The reaction mixture is gradually allowed to warm, with stirring, until reaction is complete, e.g. to −40° C. for 1 to 3 hours, then to 0° C. for 30 to 60 minutes. A detailed description of this procedure is given in Example 2.

Alternatively, a compound of Formula II may be prepared by reacting an aminoalcohol of Formula III with thionyl chloride to form the corresponding 2-oxo-1,2,3-oxathiazolidine, and then oxidizing to form a compound of Formula II. The reaction with thionyl chloride is carried out in a fashion similar to that described above for sulfuryl chloride, i.e., in the presence of a suitable base and in a suitable aprotic solvent. The reaction mixture is stirred for approximately 45 minutes at ambient temperature, refluxed for 1 hour and then stirred at ambient temperature for an additional 2 hours. A detailed description of this procedure is given in Example 3.

The oxidation is carried out in a two-phase solvent system, e.g. water/isopropyl acetate, water/methylene chloride, water/1,2-dichloroethane, or water/ethyl acetate. Appropriate oxidants include sodium bromate, sodium hypochlorite, sodium metaperiodate, chlorine, and potassium periodate, in the presence of a catalytic amount of $Ru^{+8}$ or similar transition metal catalyst. A detailed description of this procedure is given in Example 3.

Step 2

A cyclic amine of Formula I is prepared by reacting the appropriate 2,2-dioxo-1,2,3-oxathiazolidine, from Step 1, with an organometallic nucleophile, $R^1M^*$. The dioxooxathiazolidine is slowly added to a solution containing the nucleophile while maintaining a reaction temperature of −68° C. or below. Suitable solvents for the reaction include ethers such as tetrahydrofuran, methyltetrahydrofuran, etc. The reaction mixture is allowed to warm to room temperature and stirred for approximately 12 to 20 hours. The solvent is then evaporated, and the remaining crude sulfamic acid salt is hydrolyzed with aqueous acid to form the amine of Formula I, which may be isolated as the free amine or as an acid addition salt. A detailed description of this procedure is given in Example 4.

EXAMPLE 1

Preparation of Compounds of Formula III

A. (R)-2-Pyrrolidinemethanol [A compound of Formula III in which $R^2$, $R^3$ and $R^4$ are hydrogen, and n is 1]

Lithium aluminum hydride (25 g) was added over approximately 15 minutes to a 2 liter 3-neck round-bottom flask containing 1056 mL tetrahydrofuran and fitted with an addition funnel and a reflux condenser topped with a drying tube. The hydride solution was refluxed for 20 minutes. Heating was then stopped and D-proline (48.6 g; 422.1 mmol) was added in approximately 0.5 g portions over approximately 20 minutes. Remaining D-proline was washed in with 10 to 20 ml tetrahydrofuran, and the mixture was refluxed for 2 hours, after which heating was stopped. Potassium hydroxide (11.83 g in 47.3 mL water) was added dropwise to the reaction mixture over approximately 1 hour. The reaction mixture was then refluxed for 30 minutes.

Following this, heating was stopped, and approximately 50 g of Celite was added while the mixture was cooling. The mixture was then filtered through a 1' bed of Celite in a 2 liter "C" Buchner funnel. The contents of the reaction flask were washed with 10–20 mL of tetrahydrofuran and the filter cake was compressed. The filter cake was transfered back to the reaction flask, and 500 mL of tetrahydrofuran was added. The mixture was then refluxed for 20 minutes and refiltered through the same filter. The filter cake was compressed as before, and then washed twice with 50 mL of tetrahydrofuran. Using only a vacuum sufficient to effect evaporation of the tetrahydrofuran, the filtrate was concentrated on a rotary evaporator with a 30° C. water bath to yield approximately 43 g of a pale yellow oil.

The crude product was vacuum distilled through a short path head with an 80° C. to 88° C. oil bath. A nitrogen bleed was used on the vacuum pump and manometer and the vacuum was always released with nitrogen. The total distillate was collected to yield 36.2 g of (R)-2-pyrrolidinemethanol as a colorless oil, which was stored under nitrogen to avoid reaction with atmospheric carbon dioxide.

In a similar manner, (S)-2-pyrrolidinemethanol is prepared from L-proline; (RS)-2-pyrrolidinemethanol is prepared from D,L-proline; and (R)- (S)-, and (RS)-2-piperidinemethanol are prepared from D-, L-, and D,L-pipecolinic acid.

EXAMPLE 2

Preparation of Compounds of Formula II Direct Formation of the Dioxooxathiazolidine

A.

(R)-1,1-dioxo-3a,4,5,6-tetrahydropyrrolo[1,2-c][1,2,3]oxathiazolidine [A compound of Formula II in which $R^2$, $R^3$, and $R^4$ are hydrogen, and n is 1]

(R)-2-Pyrrolidinemethanol (30.22 g; 298.8 mmol), prepared according to Example 1, and 186 mL methylene chloride were added to a 1 liter, 3-neck round-bottom flask equipped with a thermometer and a 250 mL addition funnel topped with a drying tube. Pyridine (47.74 g) was added, and the solution stirred while being cooled in a dry ice/isopropanol bath until the temperature of the mixture was below −70° C. Distilled sulfuryl chloride (40.32 g; 298.7 mmol) in 124 mL methylene chloride was added over 45 minutes while maintaining the reaction temperature at or below −60° C. The reaction mixture was allowed to warm to −40° C. and held for approximately 2 hours, during which time pyridine hydrocloride began to precipitate.

The reaction mixture was allowed to warm to 0° C., at which point more pyridine hydrochloride precipitated. It was stirred for an additional 45 minutes, and 150 mL water and 310 mL hexanes were added. The two-phase mixture was transferred to a separatory funnel, and washed in with approximately 50 mL 1:2 methylene chloride/hexanes. Following separation of the phases, the aqueous phase was extracted with 25 mL methylene chloride, and the extract added to the main organic phase together with an additional 25 mL hexanes. The organic phase was sequentially washed with 150 mL 1N hydrochloric acid, 100 mL half-saturated brine, 100 mL saturated aqueous sodium carbonate, 100 mL half-saturated brine, and 100 mL saturated brine. It was then dried over anhydrous powdered $MgSO_4$ (approximately 24 g) and allowed to stand overnight.

The dried organic phase was then filtered through an "M" Buchner funnel, and the volatiles were evaporated on a rotary evaporator with a 40° C. water bath. The remaining oily residue was dried under vacuum at 40° C. and then again at room temperature to yield 35.22 g of (R)-1,1-dioxo-3a,4,5,6-tetrahydropyrrolo[1,2-c][1,2,3]oxathiazolidine as an oil, which spontaneously crystallized, m.p. 45°–46° C. The product was scraped from the flask walls, gently pulverized with a spatula, and dried again in vacuo at room temperature.

B. In a similar manner, (S)-1,1-dioxo-3a,4,5,6-tetrahydropyrrolo[1,2-c][1,2,3]oxathiazoline is prepared from (S)-2-pyrrolidinemethanol.

EXAMPLE 3

Preparation of Compounds of Formula II Indirect Formation of the Dioxooxathiazolidine (R)-1,1-dioxo-3a,4,5,6-tetrahydropyrrolo[1,2-c][1,2,3]oxathiazoline [A compound of Formula II in which $R^2$, $R^3$, and $R^4$ are hydrogen, and n is 1]

(R)-2-Pyrrolidinemethanol (1.00 g; 9.88 mmol), prepared according to Example 1, and 6 mL methylene chloride were added to a 50 mL, 3-neck round-bottom flask equipped with a reflux condenser topped with a $CaCl_2$ drying tube, an addition funnel and a magnetic stirrer. Pyridine (1.63 mL; 20.16 mmol) was added, and the solution stirred in a room temperature water bath. Thionyl chloride (1.20 g; 10.08 mmol) in 4 mL methylene chloride was added over 15 minutes and washed in with 1 mL methylene chloride. After stirring for 45 minutes at ambient temperature, the reaction mixture was refluxed for 1 hour and then allowed to cool to room temperature and stirred for an additional 2 hours. Hexanes (11 mL) was added and the mixture was stirred in a 0°-5° C. ice bath for 1 hour. After filtration to remove precipitated pyridine hydrochloride, the solvent was removed on a rotary evaporator with a 40° C. water bath to yield 1.47 g (9.88 mmol) of (R)-1-oxo-3a,4,5,6-tetrahydropyrrolo[1,2-c][1,2,3]oxathiazolidine as a brown oil.

The (R)-1-oxo-3a,4,5,6-tetrahydropyrrolo[1,2-c][1,2,3]oxathiazolidine, from the previous step, and 20 mL ethyl acetate were added to a 50 mL round bottom flask equipped with a magnetic stirrer. A catalytic amount of $RuCl_3 \cdot 3H_2O$ (a few mg) was added, followed by $NaIO_4$ (3.17 g; 14.82 mmol) in 10 mL water. The mixture was stirred vigorously for one hour. The phases were separated, and the aqueous phase was extracted with three portions (10 mL each) ethyl acetate. The combined organic phases were washed with 10 mL aqueous sodium thiosulfate, 10 mL half-saturated brine, and 10 mL brine, and then dried over $MgSO_4$. The solvent was removed on a rotary evaporator with a 40° C. water bath to yield 0.65 g (3.98 mmol) of (R)-1,1-dioxo-3a,4,5,6-tetrahydropyrrolo[1,2-c][1,2,3]oxathiazolidine as a colorless oil which crystallized spontaneously.

EXAMPLE 4

Preparation of Compounds of Formula I

A. (R)-2-(3,4-Dimethoxybenzyl)pyrrolidine [A compound of Formula I in which $R^1$ is 3,4-dimethoxyphenyl, $R^2$, $R^3$, and $R^4$ are hydrogen, and n is 3]

4-bromoveratrole (57.00 g; 262.6 mmol) in 350 mL tetrahydrofuran was added to a 1 liter, 3-neck round-bottom flask equipped with an efficient stirrer, a thermometer and a 250 mL addition funnel topped with a nitrogen/vacuum/septum cap. The mixture was stirred while the apparatus was vacuum purged five times. The flask was then cooled in a dry ice/isopropanol bath and, when the temperature of the mixture was below −74° C., 158.9 mL 1.62M n-butyllithium in hexanes under nitrogen was added at a rate such that the reaction mixture remained at or below −70° C. Upon addition of the n-butyllithium solution, the reaction mixture immediately developed an amber color. The mixture remained homogeneous for addition of the first 50 to 100 ml and then clouded, becoming thick and beige-colored. The contents of the addition flask were washed in with 10 mL tetrahydrofuran, and the reaction mixture was stirred for 30 minutes at −73° C. to −75° C. (R)-1,1-dioxo-3a,4,5,6-tetrahydropropyrrolo[1,2-c][1,2,3]oxathiazolidine (35.00 g; 214.5 mmol), prepared according to Example 2, in 120 mL tetrahydrofuran, was added over 25 minutes such that the reaction mixture remained at or below −68° C. The dry ice was removed from the isopropanol bath, and the mixture was allowed to warm slowly. As the reaction mixture approached −45° C., the solids dissolved; and the reaction temperature rose to −8° C. while the bath temperature remained at −48° C. After the reaction mixture had begun to cool again, the isopropanol bath was removed completely and the homogeneous solution was allowed to warm to room temperature and stirred overnight.

The solution was transferred to a 1 liter round-bottom flask, and the solvent evaporated on a rotary evaporator using a 40° C. water bath. Further drying in vacuo yielded 97.6 g of crude sulfamate as an oil, to which was added 400 mL of 5% hydrochloric acid. A distillation head was affixed and residual tetrahydrofuran was distilled until the head temperature reached 95° C. The distillation head was replaced with a reflux condenser, and the mixture was refluxed overnight.

The reflux condenser was replaced with a distillation head, and the mixture was steam distilled until approximately 250 mL of a two phase oil/water distillate had collected. The distilland was cooled to room temperature, filtered through a "C" Buchner funnel, and washed with water. The filtrate was extracted three times with 50 mL toluene. The aqueous phase was stirred in an ice bath and made basic by adding dropwise 43 mL 50% aqueous NaOH. The solution was cooled to room temperature, and extracted three times with 100 mL methylene chloride. The extracts were combined and filtered through a bed of sodium sulfate in a "C" Buchner funnel, and washed in with methylene chloride.

The filtrate was evaporated to dryness on a rotary evaporator using a 40° C. water bath. Further drying on a rotary evaporator using a vacuum pump yielded 40.9 g of crude (R)-2-(3,4-dimethoxybenzyl)pyrrolidine free base as a brown oil.

The oil was dissolved in 250 mL isopropanol and acidified with 15 mL 12N hydrochloric acid. The volatiles were removed on a rotary evaporator using a 40° C. water bath. The residue was dissolved in 100 mL isopropanol, and the volatiles evaporated again. This process was repeated with a further 100 mL isopropanol, and the crude product was then dissolved in 150 mL isopropanol. Charcoal (4.5 g) was added to the solution containing the crude product, and the mixture was boiled for 15 minutes. After the mixture had cooled somewhat, it was filtered through Celite and washed in well with isopropanol. The solution was concentrated on a rotary evaporator using a 40° C. water bath to yield 53.8 g of crude (R)-2-(3,4-dimethoxybenzyl)pyrrolidine hydrochloride as a viscous brown oil, which was dissolved in 100 mL isopropanol. The solution was then warmed slightly, and diethyl ether (approximately 38 mL) was added until the mixture became cloudy. The mixture was then seeded and stirred overnight.

The mixture was stirred in an ice bath for 1 hour, then filtered through a tared "M" Buchner funnel and washed in with recycled filtrate. The cake was washed in portions with 100 mL ice-cold 30:70 diethyl ether/isopropanol to remove color, then washed twice with 25 mL diethyl ether, and dried thoroughly by suction to yield 31.82 g of (R)-2-(3,4-dimethoxybenzyl)pyrrolidine hydrochloride as an off-white powder, m.p. 133.5°–135° C.

B. In a similar manner, (R)-2-(3,4-dimethoxybenzyl)pyrrolidine is prepared from (R)-1,1-dioxo-3a,4,5,6-tetrahydropyrrolo[1,2-c][1,2,3]oxathiazolidine and 4-bromoanisole.

We claim:
1. A process for preparing a cyclic amine of Formula I

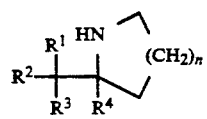
(I)

in which
R$^1$ is phenyl, optionally substituted by 1 to 3 lower alkoxy groups;
R$^2$, R$^3$ and R$^4$ are independently hydrogen or lower alkyl; and
n is 1 or 2,
which comprises
(1) Converting an aminoalcohol of Formula III

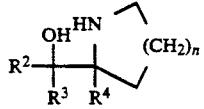
(III)

to a dioxooxathiazolidine of Formula II

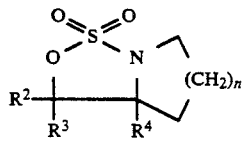
(II)

in which R$^2$, R$^3$, R$^4$ and n are as defined above; and
(2) reacting the dioxooxathiazolidine of Formula II with an organometallic nucleophile, selected from the group consisting of R$^1$Z$_n$X, R$_2{}^1$Zn, and wherein R$^1$ is as defined above, X is halogen and hydrolyzing the resulting sulfamate.

2. The process of claim 1 wherein the cyclic amine of Formula III is 2-pyrrolidinemethanol and R$^1$ is optionally substituted phenyl.

3. The process of claim 2 wherein the organometallic nucleophile is R$^1$Li.

4. The process of claim 3, wherein R$^1$ is 3,4-dimethoxyphenyl.

5. The process of claim 4, wherein the cyclic amine of Formula III is (R)-2-pyrrolidinemethanol.

6. A dioxooxathiazolidine of Formula II

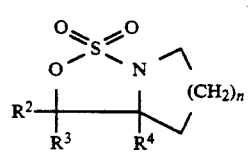
(II)

in which
R$^2$, R$^3$ and R$^4$ are independently hydrogen or lower alkyl; and
n is 1 or 2.

7. The compound of claim 6 wherein R$^2$, R$^3$ and R$^4$ are hydrogen, and n is 1, namely 1,1-dioxo-3a,4,5,6-tetrahydropyrrolo[1,2-c][1,2,3]oxathiazolidine.

8. The R-isomer of the compound of claim 7, namely (R)-1,1-dioxo-3a,4,5,6-tetrahydropyrrolo[1,2-c][1,2,3]oxathiazolidine.

* * * * *